US012791548B2

(12) United States Patent
Albuquerque et al.

(10) Patent No.: US 12,791,548 B2
(45) Date of Patent: Nov. 10, 2026

(54) SYSTEM FOR ONLINE MONITORING OF THE GRAVITATIONAL SEPARATION OF OIL EMULSIONS IN A PRESSURIZED AND HEATED SYSTEM

(71) Applicants: PETRÓLEO BRASILEIRO S.A.—PETROBRAS, Rio de Janeiro (BR); INSTITUTO DE TECNOLOGIA E PESQUISA—ITP, Aracaju (BR)

(72) Inventors: Flavio Cortinas Albuquerque, Rio de Janeiro (BR); Simonise Figueiredo Amarante Cunha, Aracaju (BR); Ayslan Santos Pereira Da Costa, Aracaju (BR); Gustavo Rodrigues Borges, Aracaju (BR); Cláudio Dariva, Aracaju (BR); Elton Franceschi, Aracaju (BR)

(73) Assignees: PETRÓLEO BRASILEIRO S.A.—PETROBRAS, Rio de Janeiro (BR); INSTITUTO DE TECNOLOGIA E PESQUISA—ITP, Aracaju (BR)

( * ) Notice: Subject to any disclaimer, the term of this patent is extended or adjusted under 35 U.S.C. 154(b) by 392 days.

(21) Appl. No.: 18/453,666

(22) Filed: Aug. 22, 2023

(65) Prior Publication Data

US 2024/0069004 A1 Feb. 29, 2024

(30) Foreign Application Priority Data

Aug. 23, 2022 (BR) ...................... 10 2022 016817 2

(51) Int. Cl.
*G01N 33/28* (2006.01)
*G01N 21/25* (2006.01)
(Continued)

(52) U.S. Cl.
CPC ....... *G01N 33/2847* (2013.01); *G01N 21/255* (2013.01); *G01N 21/8507* (2013.01);
(Continued)

(58) Field of Classification Search
CPC ............. G01N 33/2847; G01N 21/255; G01N 21/8507; G01N 35/00; G01N 2021/1734;
(Continued)

(56) References Cited

U.S. PATENT DOCUMENTS 4,345,466 A * 8/1982 Lesser ................. G01F 23/0023 73/863.82
5,128,882 A * 7/1992 Cooper .................... G01V 8/02 356/73
(Continued)

FOREIGN PATENT DOCUMENTS

CA 2310496 6/1999
CN 103913434 A * 7/2014
(Continued)

OTHER PUBLICATIONS

CN-114878513-A (Year: 2022).*
(Continued)

*Primary Examiner* — Fatemeh Esfandiari Nia
(74) *Attorney, Agent, or Firm* — Knobbe, Martens, Olson & Bear, LLP

(57) ABSTRACT

The present invention refers to an online monitoring system for the gravitational separation of oil emulsions, more specifically, a monitoring system for the properties related to the emulsions, such as the drop size distribution (DSD) and the water content (WC), simultaneously, in pressurized and heated systems at high pressures and temperatures, respectively, using near-infrared region (NIR) spectroscopy coupled with optical microscopy.
The online monitoring system is innovative as it overcomes the current need of the oil industry to remove aliquots from
(Continued)

emulsified systems under high pressure and temperature, preferably up to 70 bar (7 MPa) and 150° C., respectively, for determination of the properties of emulsions, which causes disturbances and affects the physicochemical characteristics of emulsions. Thus, the invention makes it possible to infer about the stability of the emulsions under real operating conditions by monitoring the gravitational settling of water drops dispersed in a continuous phase of oil.

17 Claims, 5 Drawing Sheets

(51) Int. Cl.

| | |
|---|---|
| ***G01N 21/85*** | (2006.01) |
| *G01N 21/17* | (2006.01) |
| *G01N 21/84* | (2006.01) |
| *G01N 35/00* | (2006.01) |

(52) U.S. Cl.

CPC ................ *G01N 2021/1734* (2013.01); *G01N 2021/8405* (2013.01); *G01N 35/00* (2013.01); *G01N 2035/00534* (2013.01); *G01N 2201/129* (2013.01)

(58) Field of Classification Search

CPC . G01N 2021/8405; G01N 2035/00534; G01N 2201/129; G01N 2015/1493; G01N 15/0205; G01N 15/1433; G01N 15/1459; G01N 2015/003; G01N 21/3577; G01N 21/359; G01N 21/85; B01D 17/00

See application file for complete search history.

(56) References Cited

U.S. PATENT DOCUMENTS

| | | | | |
|---|---|---|---|---|
| 6,115,061 A * | 9/2000 | Lieberman | G01N 21/8507 175/49 |
| 2009/0216419 A1* | 8/2009 | Shaw | G01F 23/292 73/290 R |
| 2013/0243028 A1* | 9/2013 | Singh | G01N 33/2823 374/43 |

FOREIGN PATENT DOCUMENTS

| | | | |
|---|---|---|---|
| CN | 110520712 A * | 11/2019 | G01N 21/552 |
| CN | 114878513 A * | 8/2022 | G01N 21/3554 |

OTHER PUBLICATIONS

CN-103913434-A (Year: 2014).*
CN-110520712-A (Year: 2019).*
Meyer, Tobias, et al. "Three-dimensional molecular mapping of a multiple emulsion by means of CARS microscopy."The Journal of Physical Chemistry B112.5 (2008): 1420-1426. (Year: 2008).*
Boxall, John A., et al. "Measurement and calibration of droplet size distributions in water-in-oil emulsions by particle video microscope and a focused beam reflectance method."Industrial & engineering chemistry research49.3 (2010): 1412-1418. (Year: 2010).*
Bec et al., Aug. 7, 2020, Principles and Applications of Vibrational Spectroscopic Imaging in Plant Science: A Review, Frontiers in Plant Science, 11(Article 1126): 1-27.
Borges et al., 2015, Use of near-infrared for evaluation of drop size distribution and water content in water-in-crude oil emulsions in pressurized pipeline, Fuel, 147:43-52.
Cunha et al., 2020, Multivariate regression models obtained from near-infrared spectroscopy data for prediction of the physical properties of biodiesel and its blends, Fuel, 261:116344.
Gomora-Figueroa et al., 2019, Oil emulsions in naturally fractured porous media, Petroleum, 5:215-226.
Goodarzi et al., Jan. 2019, A comprehensive review on emulsions and emulsion stability in chemical and energy industries, The Canadian Journal of Chemical Engineering, 97:281-309.
Honse et al., 2018, Emulsion phase inversion of model and crude oil systems detected by near-infrared spectroscopy and principal component analysis, Colloids and Surfaces A, 538:565-573.
Lake, ed., 2006, Petroleum Engineering Handbook, Society of Petroleum Engineers (TOC).
Ma et al., 2017, Rapid authentication of starch adulterations in ultrafine granular powder of Shanyao by near-infrared spectroscopy coupled with chemometric methods, Food Chemistry, 215:108-115.
Pu et al., Apr. 2020, Review of near-infrared spectroscopy as a process analytical technology for real-time product monitoring in dairy processing, International Dairy Journal, 103:104623.
Quelhas et al., 2014, Processamento de Petroleo e Gas, 2nd Ed. (TOC and synopsis).
Skoog et al., 2007, Principles of Instrumental Analysis, Thomson Higher Education, 529 pp.
Souza et al., Apr.-Jun. 2015, Effect of water content, temperature and average droplet size on the settling velocity of water-in-oil emulsions, Brazilian Journal of Chemical Engineering, 32(02):4550464.
Uma et al., Jun. 2018, A review of petroleum emulsions and recent progress on water-in-crude oil emulsions stabilized by natural surfactants and solids, Journal of Petroleum Science and Engineering, 165:673-690.
Wang et al., Jan. 2020,. Simultaneous detection of different properties of diesel fuel by near infrared spectroscopy and chemometrics. Infrared Physics and Technology, 104:103111.

* cited by examiner

SYSTEM FOR ONLINE MONITORING OF THE GRAVITATIONAL SEPARATION OF OIL EMULSIONS IN A PRESSURIZED AND HEATED SYSTEM

FIELD OF THE INVENTION

The present invention refers to a system to carry out the online monitoring of the gravitational separation of oil W/O (water-oil) emulsions, more specifically, it refers to a system that allows the monitoring, in real time, of the drop size distribution (DSD) and water content (WC) of oil emulsions in pressurized and heated systems, at high pressures and temperatures, respectively, using near-infrared region (NIR) spectroscopy coupled with optical microscopy.

The system of the present invention has application in the field of the petrochemical process industry, more specifically, the oil exploration and extraction market with the oil industry as a target audience.

BACKGROUND OF THE INVENTION

In recent years, there has been a broad growth in oil production in Brazil, mainly in reservoirs located in deep and ultra-deep waters. Despite trends towards decarbonization of the energy matrix, recent discoveries and the development of giant oil reserves have placed Brazil on a new geopolitically strategic level in the global energy sector. This generated technological challenges to be overcome by the scientific community in order to enable the technically, economically, and ecologically efficient production of such reserves (ANP, 2019).

The increase in oil production in Brazil is directly linked to the productive evolution of the pre-salt region, which currently represents approximately 70% of Brazilian production. This growth demands the optimization of processes, from extraction to refining, in order to increase the efficiency of offshore installations located at long distances from the mainland coast (ANP, 2019).

Considering the use of the conventional water injection strategy as an improved oil recovery method in these fields, the formation of stable emulsions appears as problematic in relation to flow assurance (GÓMORA-FIGUEROA et al., 2019). During the primary treatment, the contact of the oil with the formation and/or injection water, under intense shear, gives rise to emulsions, which may become an obstacle in the operation of a gravitational separator, because, in addition to causing problems such as control level of tanks, the accumulation of formed emulsion decreases the effective retention time, resulting in a reduction in the efficiency of the process (BRASIL et al., 2014; WANG et al., 2020).

In addition to burdening the costs of oil production and transportation, the water produced and originating from producing formations present dissolved salts that vary in concentration depending on the characteristics of the reservoir. Furthermore, the variation in the properties of these emulsions reduces the predictability of the behavior of these systems, making it difficult to dimension equipment and oil production levels, which makes the exploration of these fields risky (UMA et al., 2018; WANG et al., 2020).

In the petrochemical industry, monitoring the physicochemical properties of emulsions occurs by sampling the same during the production process. This sample collection process must take place throughout the production chain (for example, separators, pipes, tanks, and wells) and, when possible, in the reservoir. As emulsions are usually found in pressurized and heated systems along the production chain, the moment of sampling interferes with the representativeness and integrity of the system, which should be maintained until the moment of the analysis. However, this procedure can contribute to changes in the characteristics of emulsions, mainly in relation to the drop size distribution (BORGES et al., 2015).

The difficulty of quickly evaluating the stability of emulsions is also a sampling problem since an emulsion collected in the field can partially or completely separate until it arrives at the laboratory. Online monitoring of oil emulsion properties can serve as a parameter to help model, simulate, and optimize water/oil separation processes.

In this sense, the use of spectroscopy in the near-infrared region presents itself as an alternative to remedy the sampling problems of the oil industry. Through the near-infrared region (NIR) spectroscopy technique, it is possible to acquire qualitative and/or quantitative information on the interactions of electromagnetic waves with the constituents of a sample (BÉC; GRABSKA; HUCK, 2020). The method is based on emitting near-infrared radiation through the sample and then recording the light intensity through spectra (SKOOG et al., 2007). The applicability of NIR is vast and it is a fast, non-destructive, non-invasive analytical method with high penetration depth and rapid response to process conditions (M A et al., 2017; P U et al., 2020). Furthermore, NIR probes are cost-effective and can be easily installed using fiber optic cables, which makes their use suitable for severe process conditions, as these probes withstand high pressures and high temperatures.

However, studies on the application of NIR for the purpose of monitoring and controlling the properties of the oil emulsions in pressurized systems or in heated systems, mainly above 100° C., are still incipient. Although the influence of pressure and temperature factors on the stability of emulsions is known, the effect of the combination of these variables under severe conditions, on the characteristics of the emulsion is still not understood.

The state of the art does not disclose a system that allows online monitoring of the gravitational separation of oil emulsions in pressurized and heated systems by investigating the drop size distribution (DSD) and water content (WC), simultaneously, using near-infrared region (NIR) spectroscopy coupled with optical microscopy.

Document CA2310496A1, for example, refers to a computer-implemented method for online determination of the concentration in a catalyst stream from the hydrofluoric (HF) acid alkylation process containing HF acid, acid-soluble oil (ASO), water, and optionally an additive that suppresses the vapor pressure of the HF acid. The method employs near-infrared spectroscopy along with chemometric data analysis. However, said patent does not claim the use of NIR for monitoring the properties of water/oil emulsions, as well as the use of this monitoring in simultaneously pressurized and heated systems. In addition, a monitoring system consisting of a pressurized, heated cell coupled to a spectrophotometer, optical microscope and potentiometric titrator is not claimed.

The paper entitled "Use of near-infrared for evaluation of drop size distribution and water content in water-in-crude oil emulsions in pressurized pipeline" (Gustavo R. Borges, Gabriela B. Farias, Talita M. Braz, Leila M. Santos, Monique J. Amaral, Montserrat Fortuny, Elton Franceschi, Cláudio Dariva, Alexandre F. Santos; Fuel, v. 147, p. 43-52, 2015) is one of the rare reports on the application of the NIR technique in monitoring WC and DSD in pressurized systems. In this paper, a test circuit was developed containing an optical microscope connected in series with a near-infrared spectrophotometer to monitor the online system under pressure of up to 25 bar (2.5 MPa), using PLS (Partial Least Squares) calibration for properties prediction. The obtained DSD and WC data were used for NIR calibration, and the results indicated that the models obtained for the pressurized system have good predictive capacity of the emulsion properties, being able to accurately predict the WC of emulsions in situ to within 1% by mass. However, in this paper, all conditions investigated were at room temperature and it was not possible to monitor the gravitational separation of emulsions.

The paper entitled "*Emulsion phase inversion of model and crude oil systems detected by near-infrared spectroscopy and principal component analysis*" (Siller de Oliveira Honse, Khalil Kashefi, Rafael Mengotti Charin, Frederico Wanderley Tavares, Jose Carlos Pinto, Marcio Nele; *Colloids and Surfaces A: Physicochemical and Engineering Aspects*, v. 538, p. 565-573, 2018) refers to NIR and electrical conductivity techniques, where such techniques have been used to analyze the phase inversion of the crude oil emulsions based on temperature, salinity, surfactant concentration and water-to-oil ratio. The results showed that NIR spectroscopy is useful for detecting the phenomenon of inversion of emulsions and that raw spectral data can be used, with minimal chemometric treatment, when the inversion causes strong differences in NIR spectra. However, this is a work whose operational conditions of the tests were carried out at ambient temperature and pressure and without the use of an online monitoring system for these properties. Furthermore, it is not possible to monitor the gravitational separation of emulsions through the gravitational settling of the water drops dispersed in a continuous oil phase.

The paper entitled "*Multivariate regression models obtained from near-infrared spectroscopy data for prediction of the physical properties of biodiesel and its blends*" (Camilla L. Cunha, Alexandre R. Tones, Aderval S. Luna; Fuel, v. 261, p. 116344, 2020) refers to the NIR spectroscopy that was used in order to predict physicochemical properties of biodiesel and mixtures thereof. The obtained results showed that NIR spectroscopy is a valid tool to predict these parameters in biodiesel samples, with errors similar to the maximum errors allowed by the experimental error. However, all tests carried out in this study took place under conditions of ambient temperature and pressure and without the use of an online monitoring system for these properties.

From the aforementioned reports about the state of the art, it is possible to elucidate some differentials compared to the present invention, which characterize the same as new and inventive. In this sense, it is noteworthy that previous works do not monitor emulsions; more specifically, they do not monitor the gravitational settling of water drops dispersed in a continuous phase of oil and do not allow the analysis of water content along a gravitational settling system at high temperatures and pressures. Finally, it is reaffirmed that there is no prototype or similar system in the technical or scientific literature that allows both providing the above-mentioned properties and serving as a database for the calibration of near-infrared NIR tools.

SUMMARY OF THE INVENTION

The present invention aims at carrying out online monitoring of the drop size distribution (DSD) and water content (WC), simultaneously, of oil emulsions in pressurized and heated systems using spectroscopy in the near-infrared region (NIR) coupled to optical microscopy.

Another objective of the online monitoring system of the present invention is to guarantee the integrity of the samples and their real characteristics in systems emulsified under pressure, more specifically pressures up to 70 bar (7 MPa) and heated over temperatures up to 150° C. This evaluation of the characteristics of the emulsions, without disturbing the sample, allows a more accurate reading of the physicochemical properties of the emulsion, mainly with regard to the drop size distribution (DSD) of the dispersed phase (water), since oil emulsions are found in pipes under the effect of high pressure and temperature, during the exploration step.

In addition, the present invention aims at optimizing the primary oil treatment processes and, consequently, increase productivity and reduce oil production costs through the online monitoring system of the present invention.

Therefore, the invention integrates what is best in online monitoring of different properties of emulsions through the application of the NIR spectrophotometer, a fast, non-destructive, non-invasive analytical method with high depth of penetration and fast response in process conditions, thus resulting in the monitoring of what is really happening throughout the pressurized and heated process in the oil industry. In this way, it is possible to correlate the drop size distribution (DSD) and water content (WC) with the spectra obtained over time, at temperatures and pressures similar to those observed in primary oil processing plants.

BRIEF DESCRIPTION OF THE FIGURES

The present invention will be described below, with reference to the attached figures that, in a schematic way and not limiting the inventive scope, represent examples of its embodiment.

DETAILED DESCRIPTION OF THE INVENTION

The present invention describes a system for online monitoring of the gravitational separation of oil emulsions in a pressurized and heated system, as well as all the operating units of said system.

The present invention further describes all the steps and parameters involving the online monitoring of the drop size distribution (DSD) and water content (WC), simultaneously, of oil emulsions in pressurized and heated systems using spectroscopy in the near-infrared region (NIR) coupled to optical microscopy.

Figure 1:
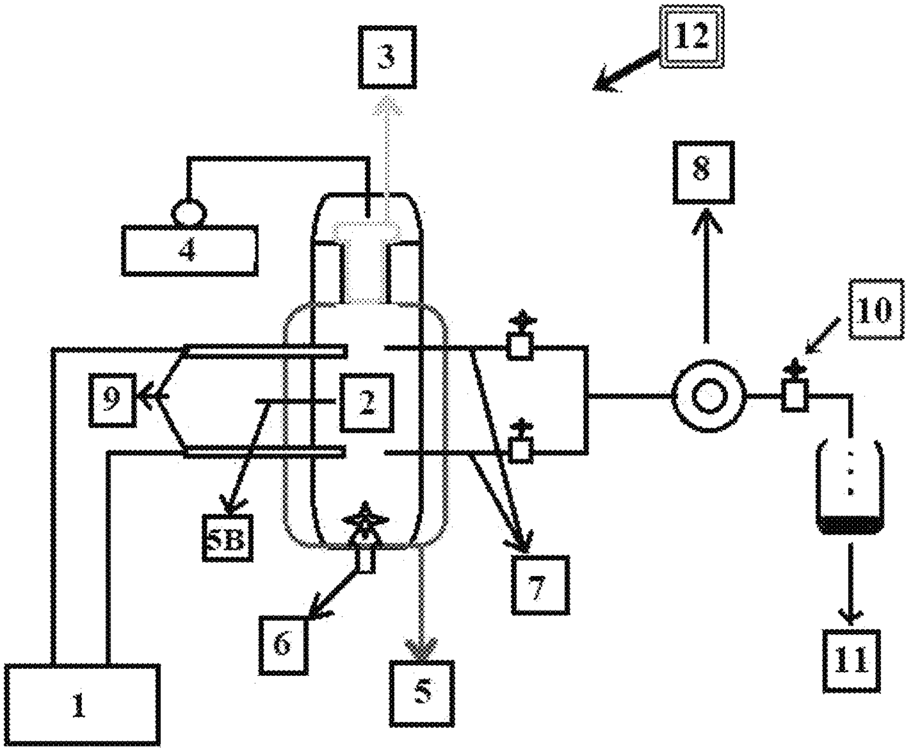
FIG. 1 illustrates a schematic diagram of the system used for online monitoring.

The online monitoring system (12), illustrated in FIG. 1, comprises NIR spectrophotometer (1); emulsion cell (2); mobile piston for pressurizing the emulsion cell (3); positive displacement pump (4) for pressure maintenance; heating unit (5, 5A and 5B); mechanical stirring unit (6) of the emulsion cell; unit of collection points (7) of the emulsion coupled to the flow chamber used in the optical microscope (8); NIR probes (9); sample collection unit (10) for analysis of the water content in a Karl Fischer potentiometric titrator (11).

Figure 2:
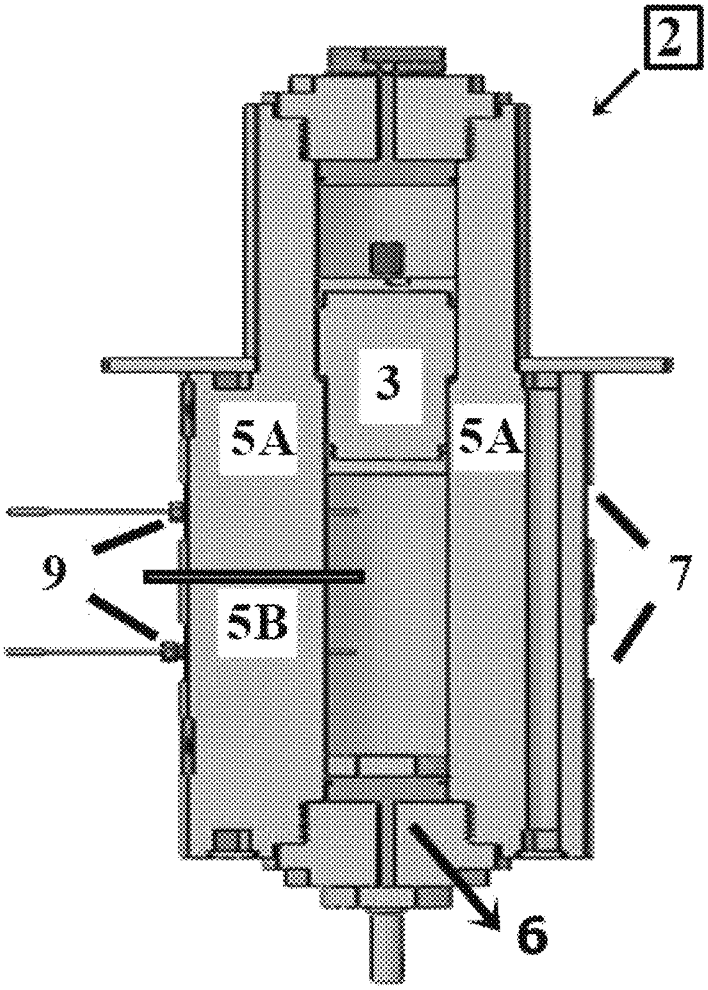
FIG. 2 illustrates the front view of the emulsion cell of the present invention.

The emulsion cell (2) of said system (12), illustrated in FIG. 2, comprises a pressurization unit with a movable piston (3), a heating unit comprising a thermostatic bath (5), a jacket (5A) for circulation of thermal fluid and thermocouple (5B), unit of collection points (7), connections for up to two NIR probes (9) and a mechanical stirring unit (6).

Operating Units of the Online Monitoring System

The online monitoring system (12) comprises an emulsion cell (2) of high pressure of variable volume, in which it is possible to attach probes (9) of an NIR spectrophotometer (1) to collect spectra of the pressurized system at high temperature.

The emulsion cell (2) has sampling points (7) to take pressurized and heated samples at high pressures and temperature, respectively, to an inverted optical microscope (8) to determine the DSD of the system and finally enable collection of samples for analysis of water content in a Karl Fischer potentiometric titrator (11). The pressurization of this cell (2) is done through a movable piston (3) located at the upper part of the cell and a positive displacement pump (4) to maintain the pressure. The cell (2) also has a heating unit through a thermostatic bath (5), a jacket (5A) for thermal fluid circulation and temperature maintenance, in addition to a thermocouple connection (5B). It should be noted that an electrical resistance heating system (not shown) coupled to the cell body can be applied, without loss of quality in the results, replacing the proposed heating unit (5, 5A and 5B). At the bottom of the cell, there is a mechanical stifling unit (6), provided with a rotor with a three-blade propeller, which allows the homogenization of the system and suspension of the emulsion drops. Along the cell body (2), there are two sampling points (7), which are directly coupled to the flow cell of the optical microscope (8), for determination of the DSD without the need to depressurize the system. The unit allows the connection of up to two NIR probes (9), thus enabling the collection of spectra at different heights along the cell body. It should be emphasized that the position of the probes (9) coincides with the sampling sites (7), so it is possible to correlate the drop size distribution (DSD) and water content (WC) with the spectra obtained over the time, at temperatures and pressures similar to those found in primary oil processing plants.

The emulsion cell (2) is made of stainless steel, has a variable volume, mechanical stirring unit (6), with a useful volume of approximately 200 mL, which allows the removal of samples from the collection point (7) without pressure change and with connections for up to two NIR probes (9). It further consists of a pressurization unit using a mobile piston (3) and a heating unit using a thermostatic bath (5), which heats the thermal fluid that circulates through the jacket (5A) around the cell (2), as well as a thermocouple connection (5B) for measuring the temperature of the cell (2). Optionally, the heating unit (5, 5A and 5B) can be replaced by the electrical resistance (not shown).

The flow cell of the optical microscope (8) is coupled to the sample collection unit (7) for determining the drop size distribution (DSD) of the emulsion under pressurized and heated conditions at high pressures and temperatures, respectively. The water content (%) is determined by the Karl Fischer potentiometric titrator (11), which is coupled to the sample collection unit (10) associated with the flow cell of the optical microscope (8).

Preparation of Water/Oil Emulsions

The synthesis was initiated by weighing 150 g of the oil of interest, in this case O2 oil, in a plastic flask with a capacity of 1 L. Next, 150 g of distilled water were added, obtaining 300 g of W/O-type emulsion. After weighing, the flask was capped and manual stirring was performed in order to incorporate the water into the oil. After the incorporation step of the dispersed phase (water), the emulsion was transferred to a 1 L glass beaker, in which shearing or homogenization of the emulsion was carried out using two stirring units. For emulsions with a minimum average diameter of 10 μm, a CAT mechanical stirrer, model R50 with adjustable speed between 0 and 1600 RPM was used. For smaller average diameter emulsions, an IKA Ultra Turrax T25 Basic high-speed stirrer with 6 speeds ranging from 6,500 to 24,000 RPM was used. In this way, the emulsions were synthesized, in laboratories, with water contents between 2% and 5% (m/m), having as reference the conditions found during the oil production.

Determination of Drop Size Distribution—DSD

To determine the DSD of the oil emulsions and subsequent NIR calibration, an inverted optical microscope (8) (Carl Zeiss, Axiovert 40 MAT) was used, provided with four objective lenses that allowed magnifications of 10, 20, 50 and 100×. The equipment is coupled to a CCD (Charge Coupled Device) video camera, which is connected to a microcomputer (not shown) provided with the Axiovision software, version 4.9.1, specific for image acquisition and processing. Over the microscope (8) a flow chamber was positioned, made of stainless steel, provided with two glass lenses with a diameter of 3.9 cm and a thickness of 0.8 cm, this chamber (not shown) being able to work under pressure and heating through the use of a heating mantle (not shown).

To obtain the DSD, 10 (ten) images were captured every 30 minutes of monitoring in static mode, in the pressurized and heated system, at different points of the lens of the flow camera, using the optical microscope (8). Then, 5 (five) images were randomly selected for each monitoring time, and the diameters of all identifiable water drops were marked. Subsequently, the volumetric diameter (D(4.3)) (μm) and the diameter median (D(0.5)) (μm) were determined at each collection time.

Spectra Collection Process

To obtain the NIR spectra, a transflectance probe containing an adjustable optical path from Hellma, model Falcata, whose operating limits are 150° C. and pressure of 35 bar (3.5 MPa) was used. The probe (9) was connected, through optical fibers, to a near-infrared (NIR) spectrophotometer, manufactured by Bruker, model MPA, which has three measurement modules, two of which being internal measurement channels regarding the device, and another external measurement module via probes and fiber optics (capable of connecting two probes).

During the online monitoring of the emulsions, the spectra were collected in an interval of 30 minutes in a process of 16 scans, each scan with a resolution between 1 and 32

$cm^{-1}$, preferably 8 $cm^{-1}$ in the entire wavelength region corresponding to the NIR (4000 to 12000 $cm^{-1}$). The measurements were performed at the equipment usual intensity, with processing and visualization performed using the OPUS 7.5 software available with the NIR analyzer.

Water Content Determination Process

At predefined time intervals, typically every 20 or 30 minutes of monitoring, after determining the DSD and collecting NIR spectra, aliquots of approximately 5 to 10 mL were taken from the system to determine the representative water content of that moment of analysis. These aliquots were submitted to potentiometric titration using Karl Fischer reagent (Metrohm, 870 KF Titrino Plus). The analyses were performed in triplicate.

Online Monitoring Process of System Properties (WC and DSD) Using the Proposed System The online monitoring process begins with closing the emulsion cell by inserting mobile components such as NIR probes (9), stirring system (6), connecting the thermocouple (5B) and the lines of collection at the sampling points (7). After that, the emulsion of interest is fed into the cell (2), the stirring unit (6) is activated, the system is pressurized, by using the mobile piston (3), typically up to 20 bar (2 MPa) and constant maintenance of this pressure through the positive displacement pump (4) and adjustment of the system temperature (80 to 120° C.) through the use of a thermostatic bath (5), a jacket (5A) for circulation of thermal fluid and thermocouple (5B) and, optionally, an electrical resistance (not shown).

After stabilizing the pressure and reaching the desired temperature (they are kept constant throughout the procedure), the stifling unit is turned off and the process of monitoring the gravitational settling of the drops begins by obtaining the properties of the system (WC and DSD) every 30 minutes, online and without disturbances. This procedure aims at monitoring changes in DSD and WC of the emulsion over time and allows inferences about the stability of emulsions under such conditions. This procedure is completed after using the entire useful volume of the emulsion cell (2), which is approximately 200 mL.

It should be emphasized that gravitational separation experiments can be carried out at temperatures up to 150° C., preferably, in the ranges of 80 to 150° C., 80 to 120° C., 80 to 100° C., at pressures up to 70 bar (7 MPa), preferably, in the ranges from 10 to 70 bar (1 MPa to 7 MPa), 10 to 60 bar (1 MPa to 6 MPa), 10 to 50 bar (1 MPa to 5 MPa), 10 to 40 bar (1 MPa to 4 MPa), 10 to 30 bar (1 MPa to 3 MPa) and 10 to 20 bar (1 MPa to 2 MPa) with oil emulsions having water contents up to 50%, preferably in the ranges 2 to 10%, 2 to 20%, 2 to 30%, 2 to 40% and 2 to 50% and average drop size of up to 70 μm, preferably in the ranges 5 to 70 μm, 5 to 60 μm, 5 to 50 μm, 5 to 40 μm, 5 to 30 μm, 5 to 20 μm and 5 to 10 μm.

Each validation experiment of the proposed system was carried out at high and fixed temperature and pressure, and it was possible to monitor the behavior of the water content over time, collecting samples, also with the objective of verifying the distribution of the water content over time along the entire length of the cell (2) and monitor the phase separation of the emulsion. The results obtained from this monitoring are shown in FIG. 3.

With this monitoring, a decrease in water content was observed along the cell body, from top to bottom, during the experiment, given that water drops have a higher density than oil and, due to the action of gravity, tend to settle (GOODARZI AND ZENDEHBOUDI, 2019; LAKE, 2006; SOUZA et al., 2015). It is important to emphasize that the initial and theoretical water contents are altered by the pressure and temperature conditions to which the emulsions are submitted. In addition, it is considered as the initial monitoring time the moment when the system reaches the operating pressure (20 bar-2 MPa) and the test temperature (80 to 120° C.); in this time interval of pressurization and heating, alterations may occur to the water content contained at the top and bottom of the emulsion cell, differing from the initial water content of the emulsions prepared and inserted into the unit.

Figure 3:
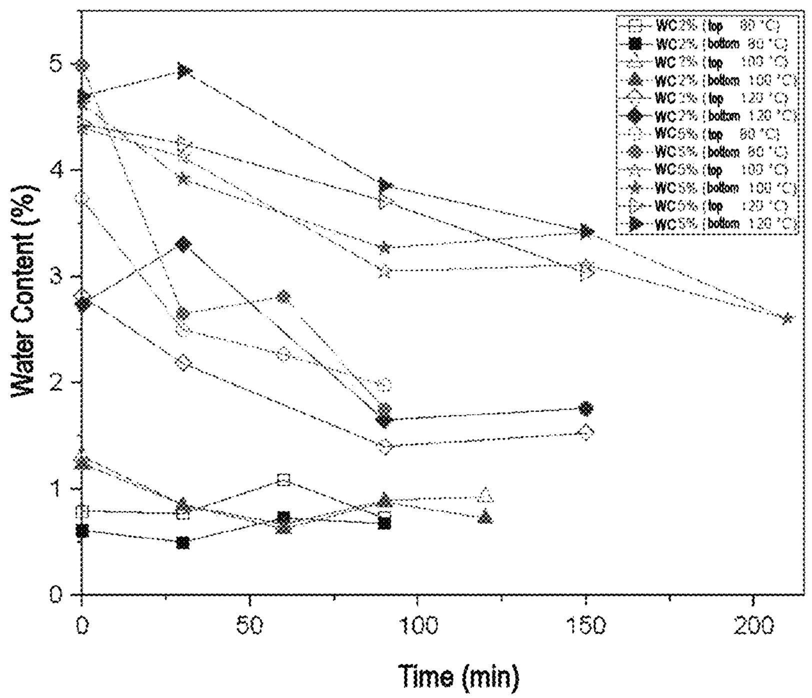
FIG. 3 illustrates the graph referring to the monitoring of water content (%) in emulsions versus time along the length of the emulsion cell.

FIG. 3 shows the behavior of water content along the length of the cell of emulsions at different times. For the theoretical water content of 2%, a rapid decrease is observed shortly after pressurizing and heating the system, and then the WC values remain practically constant until the end of the experiments. As for the emulsions with an initial water content of 5%, there is a gradual decay of the water content at the two collection points, where it is possible to observe the kinetics of movement of the water layer towards the bottom of the cell.

It is worth noting that, at the end of the monitoring experiments, after opening the emulsion cell, it was found in some situations the presence of free water, resulting from the phase separation of the W/O emulsion. This phenomenon was expected, since the increase in pressure and temperature accelerate the phase separation. However, it is important to emphasize that the free water formed below the collection point located at the bottom of the monitoring cell (2), and it is not possible to quantify this phase by the system.

Figure 4:
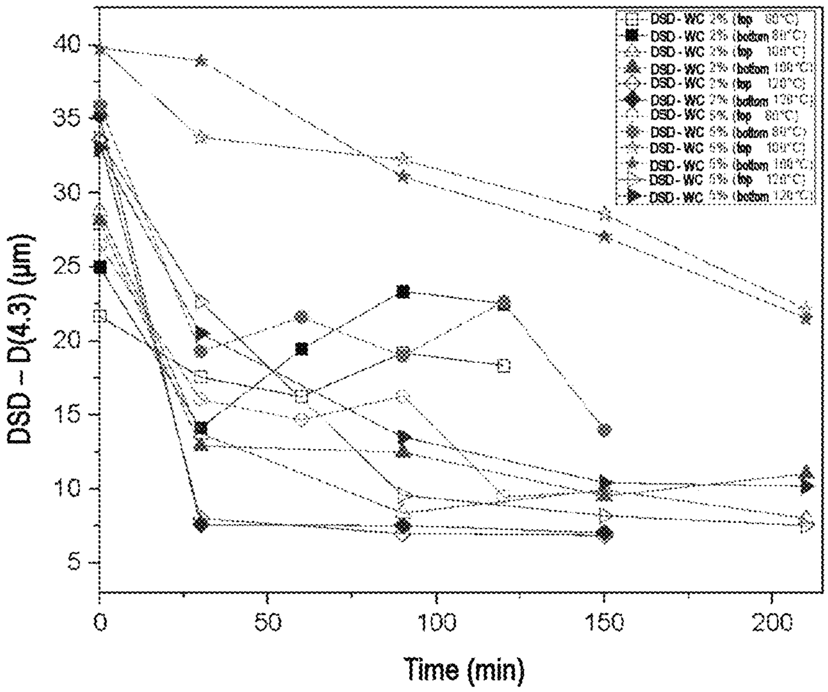
FIG. 4 illustrates the graph referring to the monitoring of DSD (μm) in emulsions versus time along the length of the emulsion cell.

The behavior of DSD over time was also monitored through the system of the present invention. In this sense, emulsion samples were collected in the sampling unit (7), coupled to an optical microscope (8), with the objective of verifying the drop size distribution, at different times, along the cell and monitoring the separation of emulsion phases. The results obtained from this monitoring are shown in FIG. 4.

For the temperature of 80° C., in both tests with 2 and 5% of water, it was observed that the DSD of the top of the cell was lower than that of the bottom throughout the experiment. This behavior is due to the coalescence and settling of water drops over time. As for the temperatures of 100° C. and 120° C., it was observed that the DSD decreased rapidly over the time of the experiment, both at the top and at the bottom of the cell. According to Lake (2006) and Goodarzi and Zendehboudi (2019), the increase in temperature leads to a reduction in the viscosity of the oil (continuous phase), which favors the collision of the emulsified drops and promotes an increase in the frequency of collision and coalescence, leading to a fast phase separation. This phase separation was also verified by the formation of free water in the lower part of the emulsion cell (2), observed for all temperatures and water contents.

The results presented so far demonstrate the ability of the system to monitor the stability of emulsions in pressurized systems heated to high temperature, by monitoring the gravitational separation of the emulsion.

Calibration of the Monitoring Models

The data obtained during the monitoring of the properties, water content and DSD, together with the spectra collected simultaneously, make up the necessary database for the calibration, with the objective of developing a chemometric model to relate the NIR spectrum with the system properties at that instant (real time). This step involves the use of multivariate calibration algorithms, preferably PLS algorithms, to predict the value of a parameter or property of interest, in this case, the WC and the DSD. The prediction models used in the system of the present invention, obtained by the PLS chemometric technique, whose operational conditions are arranged according to the location of the monitoring probe used in the emulsion cell (2) can have their application expanded to oil pipelines or tanks in conditions of pressure and temperature similar to, but not limited to, the system in question.

The NIR spectrophotometer, model MPA from Bruker, has the OPUS QUANT2® software, which was used to calibrate the chemometric models for monitoring the system. The objective of this step was to develop and validate the algorithms of the chemometric models. Initially, the spectra were pre-treated in order to remove systematic variations that are not explained by the variation of the monitored property, such as random noise.

In view of the spectral regions and the different pre-treatment methods, it is necessary to choose which method or methods best fit the obtained data. To this end, the OTIMIZAR tool was used, available in the OPUS software itself, which scans the spectrum regions and applies the available pre-treatments, with the objective of finding the smallest number of factors (latent variables) that provide the best correlation between the spectrum and the property to be identified. Partial Least Squares (PLS) regression was used in order to find an optimal number of latent variables that provide the best fit.

After the calibration, the efficiency that the PLS model has in predicting the reference values (WC and DSD) was calculated using two key metrics for error analysis: the square root of the mean standard error (Root Mean Squared Error—RMSE) and the coefficient of determination ($R^2$), presented in Equations 1 and 2, respectively.

$$RMSE = \sqrt{\frac{1}{M} \cdot \sum_{1}^{M} \left(Y_i^{exp} - Y_i^{pred}\right)^2} \quad \text{(Equation 1)}$$

$$R^2 = 1 - \frac{\sum_{1}^{M} \left(Y_i^{exp} - Y_i^{pred}\right)^2}{\sum_{i=1}^{M} \left(Y_i^{exp} - \underline{Y}\right)^2} \quad \text{(Equation 2)}$$

where M represents the number of analyzed samples;

$$Y_i^{pred}$$

represents the i-th value predicted by the model and $$Y_i^{exp}$$

represents the i-th value obtained through experimental analysis (reference values); and Y is the mean of all experimentally measured values.

For the fitting of the PLS model, through cross-validation, which checks the model repeatedly, removing one or more samples from the estimation model and then trains the model with the remaining data in order to optimize the estimated parameters, Standard error (SE) and Mean Squared Error (MSE) were used, presented in Equations 3 and 4, respectively. This procedure allowed, for the PLS, both the determination of the optimal number of factors and also the dimensions of the components at the moment of fitting.

$$SE = \sqrt{\frac{1}{M - 1 - h} \cdot \sum_{1}^{M} \left(Y_i^{exp} - Y_i^{pred}\right)^2} \quad \text{(Equation 3)}$$

$$MSE = \frac{1}{M} \cdot \sum_{1}^{M} \left(Y_i^{exp} - Y_i^{pred}\right)^2 \quad \text{(Equation 4)}$$

After the optimization process (error minimization), the RMSE was used as an indicator to evaluate whether the model is satisfactory or not. In addition to being used as an objective function for minimizing the error and estimating the parameters, it is also possible to use the SECV error as a diagnostic criterion for the modeling. Its value should not greatly exceed the standard deviation of the experimental technique used in the reference measurements.

To fit the DSD models, approximately 430 spectra collected in the emulsion cell (2) were used. The spectra, after pre-treatment, were used to relate to the DSD values obtained after the above-mentioned analyses, using the PLS technique.

Figure 5:
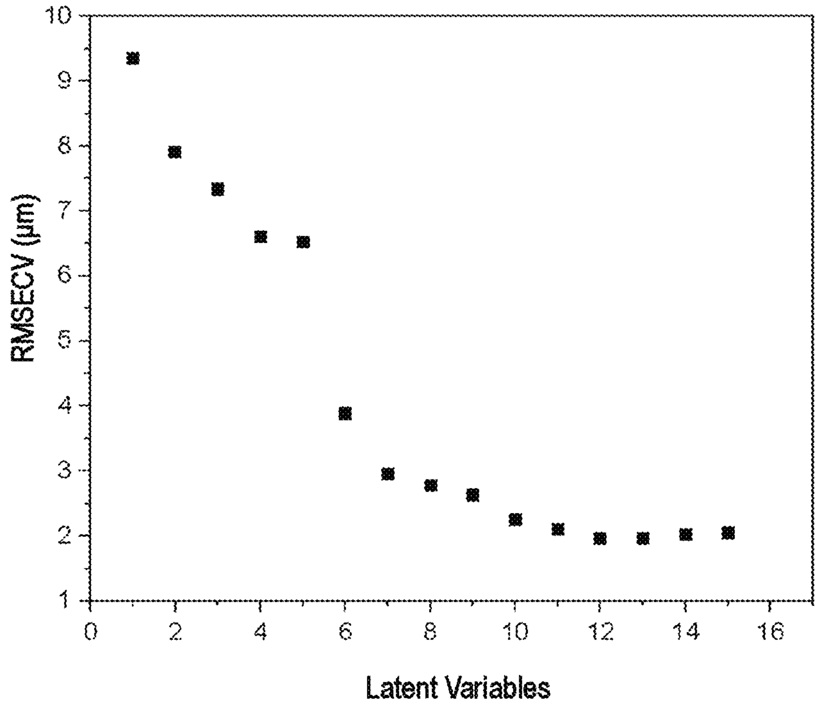
FIG. 5 illustrates the graph referring to the standard error of cross validation (RMSECV) for DSD (D(4.3)) (μm) of the PLS model at 20 bar (2 MPa) of pressure.
Figure 6:
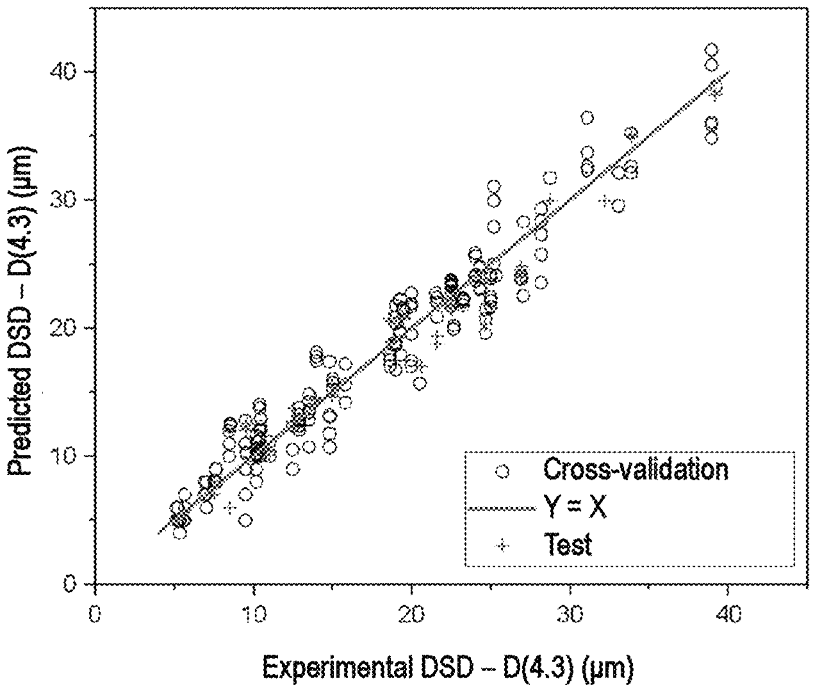
FIG. 6 illustrates the graph referring to the values predicted by the DSD model—D(4.3) (μm) on the experimental values of DSD—D(4.3) (μm) referring to the cross-validation data for the model built with spectra collected through the system of the present invention.

FIG. 5 shows the trend of the cross-validation standard error (RMSECV) for DSD (D(4.3)) (μm) at 20 bar (2 MPa) pressure when a cross-validation test was performed. The minimum value of RMSECV was reached when 12 latent variables were used. FIG. 6 shows the relation between the DSD predicted by the model and the experimental DSD.

In the model calibration step, the results were a fit $R^2$ of 0.98 and RMSEE 1.39 μm. The model for the DSD reached a coefficient of determination ($R^2$) of 0.95 between the DSD predicted by the model and the experimental DSD in the cross-validation with error (RMSECV) of 1.96 μm, values obtained with 12 latent variables at the temperatures of 80, 100 and 120° C. As for the model test step, an $R^2$ of 0.95 and an error (RMSEP) of 1.81 μm were obtained. Therefore, the model proposed herein by the inventors (under conditions of high pressure and temperature) presented an RMSEP of 3.8 for a range of D(4.3) from 9.9 to 41.5 μm and $R^2$ of 0.86, these data being superior and with a wider range of application to those known in the state of the art.

To fit the water content models, the same spectral database used in the previous step of fitting the DSD models was used. The spectra, after the pre-treatment, were used to correlate with the respective WC values obtained in the Karl Fischer analyses using the PLS technique.

Figure 7:
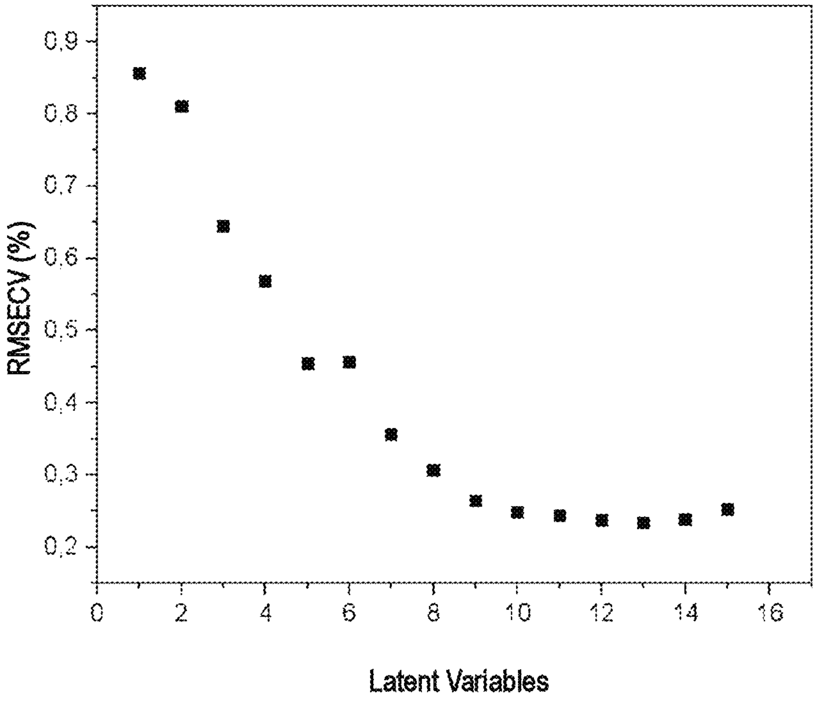
FIG. 7 illustrates the graph referring to the cross-validation standard error (RMSECV) for WC (%) of the PLS model at 20 bar (2 MPa) of pressure.
Figure 8:
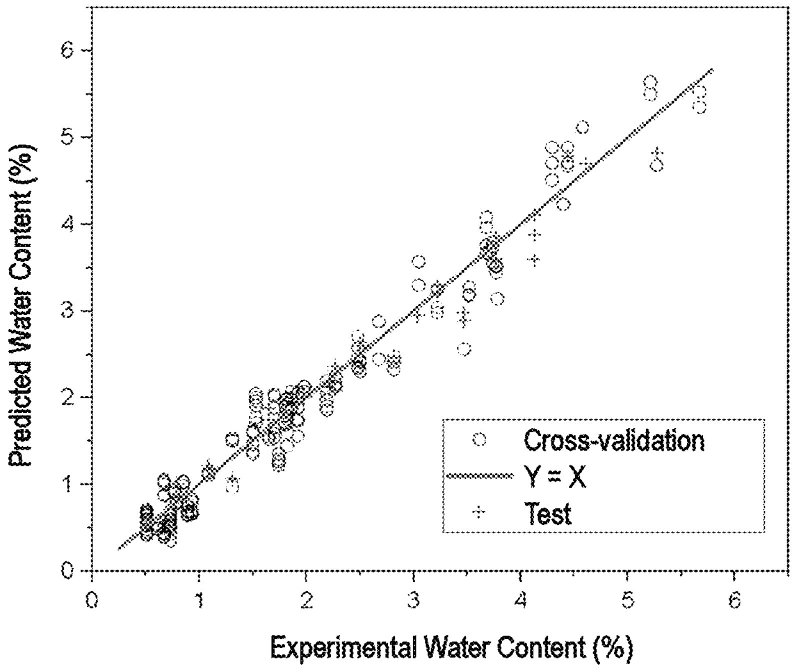
FIG. 8 illustrates the graph referring to the values predicted by the model of water content (%) on the experimental values of water content (%) referring to the cross-validation data for the model built with spectra collected through the system of present invention.

FIG. 7 shows the trend of the cross-validation standard error (RMSECV) for WC at 20 bar (2 MPa) pressure when a cross-validation test was performed. As can be seen, a minimum value of RMSECV was reached when 11 latent variables were used. FIG. 8 shows the relation between the WC predicted by the model and the experimental WC.

In the calibration step of the PLS model for water content, a fitting $R^2$ of 0.99 and RMSEE 0.16% were obtained. For the validation step, a coefficient of determination ($R^2$) of 0.96 was reached between the WC predicted by the model and the experimental WC in the cross-validation with error (RMSECV) of 0.24%, values obtained with 11 latent variables in the temperatures of 80, 100 and 120° C. For the model test step, an $R^2$ of 0.97 and a standard error (RMSEP) of 0.23% were obtained.

Accordingly, the potentiality of monitoring the WC in a range of 0.5 to 6% and DSD, in a range of 5 to 40 μm, of the system in question is evident, using NIR spectra, with PLS as a promising algorithm for model fitting.

Example of Embodiment

The online monitoring process of the experiment of the present invention began with the insertion of the NIR probes (9), connection of the thermocouple (5B), and the feeding of the emulsion of interest into the cell (2) with contents initial 2% or 5% water. Next, the stirring unit (6) is activated, system pressurization up to 20 bar (2 MPa) and constant maintenance of this pressure through the positive displacement pump (4) and adjustment of the system temperature to 80, 100 or 120° C. (temperatures kept fixed throughout each experiment) through the use of a thermostatic bath (5), a jacket (5A) for circulation of thermal fluid and thermocouple (5B). After stabilizing the pressure and reaching the temperature of interest, the stirring unit (6) was turned off, which aims at keeping the emulsion homogeneous and the suspension of water drops during the moment of pressurization and heating. The process of measuring the stability of the emulsion occurred by monitoring the gravitational settling of the drops by obtaining the system properties (WC and DSD), whose values of these properties were obtained through the NIR spectra simultaneously and with a programmable time interval according to with the need of the operator. However, for purposes of demonstrating the functionality of the present invention, the present experiment presents results obtained in monitoring done every 30 minutes online and without disturbances. With this monitoring, a decrease in the water content along the body of the emulsion cell (2) during each test was expected, given that the drops have a higher density than the oil and, due to the action of gravity, tend to settle. The initial and theoretical water contents are altered by the pressure and temperature conditions to which the emulsions are submitted. The initial online monitoring time was considered the moment when the system reached the operating pressure (20 bar (2 MPa)) and the test temperature (normally between 80 and 120° C.); in this short interval of time of pressurization and heating, alterations occurred to the water content along the body of the cell (2), differing from the initial water content of the emulsions prepared and inserted into the unit.

FIG. 3 shows the monitoring of water content along the length of the emulsion cell (2). For the theoretical water content of 2%, a rapid decrease occurred shortly after pressurizing and heating the system, and then the WC values remained practically constant until the end of the tests. As for the theoretical water content of 5%, the water content decay at the two collection points was more gradual, and it was possible to observe the kinetics of movement of the water layer towards the bottom of the cell. With the use of the monitoring system, it was also possible to identify phase separation and formation of free water, after opening the emulsion cell (2). This phenomenon was already expected since the increase in pressure facilitates phase separation.

The specialized literature indicates that the behavior of the DSD of emulsified systems (FIG. 4) is dynamic. Thus, with the passing of the test time, it is expected that the drops will settle or coalesce, that the DSD in the initial times will be greater than in the final times, since the large drops separate quickly and, in addition, that the DSD measured at the point of upper collection of cell (2) will be smaller than the DSD of the lower collection point, since, due to the action of gravity, the drops tend to settle.

For the temperature of 80° C., for both situations of water contents (2% and 5%), the expected behavior occurred and this decrease in DSD was gradual. As for the temperatures of 100° C. and 120° C., the DSD decreases rapidly over the test time, a behavior also expected, since the increase in temperature leads to a reduction in the viscosity of the oil, which favors the collision of the emulsified drops and promotes an increase in the frequency of collision and coalescence, leading to a more intense separation between the phases. The phase separation of the emulsions can be observed through the formation of free water, after opening the emulsion cell.

It should be highlighted that, in the proposed system, all these separation phenomena can be monitored online through the use of the NIR spectrophotometer together with the fitted chemometric models. In addition, the monitoring system can be readily applied in real process situations (gravitational separator vessels, for example) that are operating with the same oil, for which the system was calibrated. If the oil is different, new fittings in the chemometric models may be necessary.

In view of the facts reported above, it is possible to conclude that pressurized and heated systems at high pressures and temperatures, respectively, have a direct correlation with the stability of oil emulsions, influencing the gravitational separation of emulsions. However, it should be noted that the present invention showed that none of the works presented in the state of the art describes a clear proposal to investigate these variables. Furthermore, it is identified that there is still no available system to evaluate these properties (WC and DSD) in the way presented in the present invention.

With the invention presented herein, it will be possible to infer about the stability of emulsions under real process conditions (high pressure and high temperature). In this system, it becomes possible to monitor the gravitational settling of the water drops dispersed in a continuous oil phase under real process conditions. It is by means of this monitoring that it becomes possible to infer about the stability of the emulsion under study.

The system is versatile and allows working with different emulsions and a wide range of pressures and temperatures, making it possible to simulate different steps of oil processing. In addition, it becomes possible to evaluate the effectiveness of chemical additives under real process conditions, which will optimize the use of these products and, consequently, will make the process more profitable and will reduce the environmental impact caused by the activity.

What is claimed is:

1. A system for online monitoring of the gravitational separation of oil emulsions through their properties, wherein the system comprises:

- a near-infrared region (NIR) spectrophotometer,
- an emulsion cell,
- a mobile piston,
- a positive displacement pump,
- a heating unit,
- a mechanical stirring unit,
- an optical microscope comprising a flow chamber,
- a sample collection point unit of the emulsion coupled to the flow chamber in the optical microscope, the sample collection point unit comprising a first collection point at a first collection point height and a second collection point at a second collection point height, wherein the first and second collection points are coupled to the flow cell of the optical microscope,
- a first NIR probe coupled to the flow chamber in the optical microscope at a first height coincident with the first collection point height,
- a second NIR probe coupled to the flow chamber in the optical microscope at a second height coincident with the second collection point height, and
- a sample collection unit coupled to a potentiometric titrator, wherein an oil emulsion is under conditions of temperature between 80 and 150° C. and a pressure between 10 and 70 bar.

2. The system of claim 1, wherein the system is configured to simultaneously monitor the properties of drop size distribution (DSD) and water content (WC) of the oil emulsion.

3. The system of claim 2, wherein the NIR spectrophotometer comprises a transflectance probe having an adjustable optical path and an NIR analyzer having a wavelength between 4000 and 12000 $cm^{-1}$ and with resolution between 1 and 32 $cm^{-11}$.

4. The system of claim 3, further comprising one or more processors configured to use Partial Least Squares (PLS) models to predict the values of DSD and WC in conditions of temperature between 8° and 120° C. and pressure of up to 35 bar.

5. The system of claim 4, wherein the NIR spectrophotometer is configured to collect NIR spectra at different heights, which coincide with a collection points of the sample correlating the variation in the size of drops and water content with the spectra obtained over time under the same conditions of high temperatures and pressures.

6. The system of claim 1, wherein the emulsion cell is pressurized at high pressure through the mobile piston and has a variable volume of up to 200 mL.

7. The system of claim 6, wherein high pressure of the emulsion cell is maintained through the positive displacement pump.

8. The system of claim 7, wherein the high pressure of the emulsion cell is preferably maintained at 35 bar.

9. The system of claim 1, wherein the emulsion cell further comprises a thermostatic bath, a jacket, for circulation of thermal fluid and a thermocouple to maintain a temperature in the emulsion cell.

10. The system of claim 9, wherein the emulsion cell further comprises electrical resistors coupled to the emulsion cell, the electrical resistors configured to maintain the temperature in the emulsion cell.

11. The system of claim 10, wherein the thermostatic bath and jacket are configured to maintain a temperature from 80 to 120° C.

12. The system of to claim 1, wherein the mechanical stirring unit is located at the bottom of the cell and comprises a rotor with a three-blade propeller.

13. The system of claim 1, wherein the optical microscope is configured to determine the drop size distribution (DSD) property of the emulsion under pressurized conditions.

14. The system of claim 1, wherein the flow cell of the microscope is coupled to the sample collection unit and wherein the potentiometric titrator is configured to determine the water content of the oil emulsion.

15. The system of claim 1, wherein stirring unit is configured to maintain the homogeneous emulsion and the suspension of water drops in the emulsion cell.

16. The system of claim 1, wherein the NIR spectrophotometers are configured to take NIR spectra every 30 minutes through 5 mL aliquots, and approximately 40 mL of emulsion are used in each monitoring interval until the entire useful volume of the emulsion cell of 200 mL is used.

17. The system of claim 1, wherein the oil emulsion has a water content of up to 50% and an average drop size between 5 and 10 μm.

* * * * *